United States Patent [19]
Brossman, Jr.

[11] Patent Number: 4,566,450
[45] Date of Patent: Jan. 28, 1986

[54] DEVICE TO DISCOURAGE GROWTH OF RESPIRATORY VIRUSES

[76] Inventor: Harold A. Brossman, Jr., 4249 Kutztown Rd., Temple, Pa. 19560

[21] Appl. No.: 580,254

[22] Filed: Feb. 15, 1984

[51] Int. Cl.⁴ ............................................. A61M 15/00
[52] U.S. Cl. ........................... 128/200.11; 128/203.27; 261/DIG. 65
[58] Field of Search ....................... 128/200.11, 200.13, 128/203.16, 203.17, 203.26, 203.27, 204.17; 261/DIG. 65, 121, 142

[56] References Cited

U.S. PATENT DOCUMENTS 422,411  3/1890  Hobbs ............................ 128/203.26

FOREIGN PATENT DOCUMENTS 90023   7/1921   Switzerland ................. 128/200.11
12431   of 1895  United Kingdom .......... 128/203.26
206925  11/1923  United Kingdom .......... 128/203.26
317213  8/1929   United Kingdom .......... 128/204.17

Primary Examiner—Henry J. Recla

[57] ABSTRACT

A device for delivering humidified air at a specific optimal temperature to the nose and throat via a breathing tube and face mask for purpose stated in title; air is simultaneously heated and humidified by being bubbled thru water raised to a specific temperature by a resistance-type heating element controlled by a thermostat. Intake and exhaust valves in the face mask control direction of air flow, and an adjustable air intake tube is provided to facilitate inspiration for those with compromised lung function.

1 Claim, 1 Drawing Figure

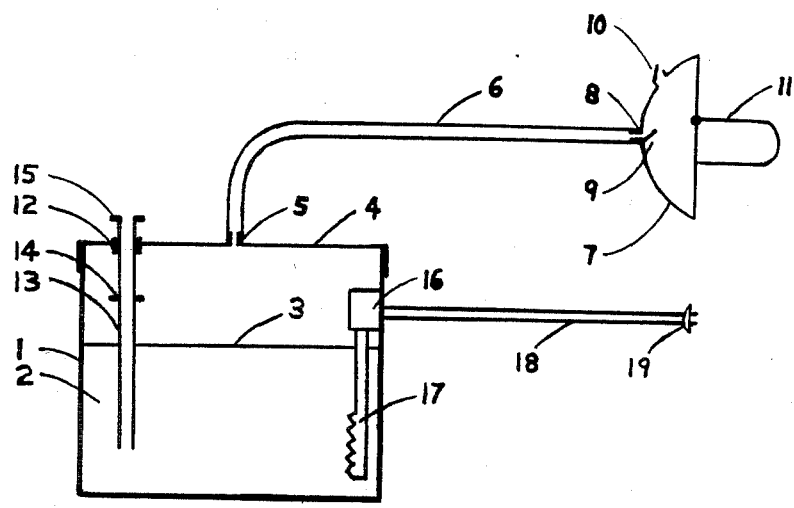

DEVICE TO DISCOURAGE GROWTH OF RESPIRATORY VIRUSES

BACKGROUND OF THE INVENTION

Checking thru the patents and cross-references for subclasses 128/203.17, 203.27, 204.17, 200.11, and 205.29 as well as D24/62, one encounters a variety of room humidifers, vaporizers, and medicinal evaporators to be used to relieve nasal congestion but nothing like my device which delivers humidified air at a specific optimal temperature thru a breathing tube and face mask for the primary purpose of discouraging the growth of respiratory viruses. My invention is designed to make use of the knowledge unknown until relatively recently that respiratory viruses prefer temperatures approximately 15° to 20° below normal body temperature (98.6°) and thrive only with difficulty at elevated body temperatures. One need only note the relative scarcity of colds in the summertime to confirm the validity of that knowledge. It is, of course, necessary to humidify the inspired air to prevent drying out and irritating the mucus membranes of the nose and throat at the elevated temperature employed, especially since the inside air in the wintertime is relatively low in humidity to begin with.

SUMMARY OF THE INVENTION

My device, unlike the decongestant devices that preceded it, is designed to discourage the growth of respiratory viruses by delivering humidified air at a specific optimal temperature (108° F.) through a breathing tube and face mask. The inspired air is simultaneously heated and humidified by being drawn as air bubbles thru water heated by a resistance-type heating element controlled by a thermostat.

Unlike its predecessors, this device does not produce steam or medicinal vapor for breathing because live steam can injure the delicate nasal lining, while medicinal vapor is essentially useless since respiratory viruses are unaffected by even the most potent antibiotics.

This device also differs from its predecessors in that it does not use a pump, air tank, steam pressure, or any other pressurized means of operation; it is operated solely by the lung power of the user. An adjustable air intake tube is provided to facilitate inspiration for the elderly or people with emphysema. When the air intake tube is raised, somewhat less humidification of the air results, but inhalation is made easier.

The face mask contains the intake & exhaust valves needed to control air flow and is readily detachable from the breathing tube so that it can be easily sanitized to prevent the spread of viruses from one user to another.

By utilizing a 12 V. heating element, a mobile version of this device can be made for use in an automobile.

DESCRIPTION OF THE DRAWINGS

Only 1 drawing is provided—a descriptive diagram.

DESCRIPTION OF THE PREFERRED EMBODIMENT

Container 1 is filled with water 2 up to the water level mark 3 on its side and is covered by a detachable lid 4 containing a tubular extension 5 to which is attached breathing tube 6 the other end of which is attached to face mask 7 via a tubular extension 8 on the mask. The mask contains an intake valve 9 and an exhaust valve 10 and an elastic band 11 to hold the mask against the face.

In the lid there is a bushing 12 in which the air intake tube 13 slides up and down thru a range limited by stops 14 & 15. A thermostat 16 controls the power fed to a 110 V. or 12 V. resistance-type heating element 17 thru power cord 18 and plug 19.

What I claim is:

1. An inhalation device for delivering heated and humidified air to a user at an optimum temperature of 108° F. comprising a container for holding a predetermined depth of water, an electric resistance type water heating element mounted in said container below the water level, air-bubbling means in said container, said container having a detachable lid with first and second ports therethrough, said air bubbling means comprising an air intake tube slidably mounted in said first port and having a first end extending above said lid and a second end extending into said container below the water level wherein said air intake tube is adjustable to permit easier inspiration with somewhat less humidification if desired, a breathing tube having a first end attached to said second port and a second end, a cleanable facemask detachably connected to the second end of said breathing tube, said facemask also having inhalation and exhalation valve means for directing the flow of air from said breathing tube, through the facemask and into the surrounding atmosphere, an elastic headband mounted on said facemask for holding the facemask to the head of a user, and thermostat means mounted in said container above the water level for regulating the heater such that air drawn into said container through said air intake tube and bubbled through said water would be delivered to the nose and throat of a user at an optimum temperature of 108° F.

* * * * *